(12) United States Patent
Uber, III

(10) Patent No.: US 11,717,605 B2
(45) Date of Patent: *Aug. 8, 2023

(54) SYSTEM AND METHOD FOR DELIVERING A FLUID WITH A CONSISTENT TOTAL VOLUMETRIC FLOWRATE

(71) Applicant: BAYER HEALTHCARE LLC, Whippany, NJ (US)

(72) Inventor: Arthur Uber, III, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 149 days.

This patent is subject to a terminal disclaimer.

(21) Appl. No.: 17/177,954

(22) Filed: Feb. 17, 2021

(65) Prior Publication Data

US 2021/0187186 A1    Jun. 24, 2021

Related U.S. Application Data

(62) Division of application No. 16/346,219, filed as application No. PCT/US2017/062728 on Nov. 21, 2017, now Pat. No. 10,933,186.

(Continued)

(51) Int. Cl.
    *A61M 5/00*      (2006.01)
    *A61M 5/168*      (2006.01)
    (Continued)

(52) U.S. Cl.
    CPC ........ *A61M 5/007* (2013.01); *A61M 5/16827* (2013.01); *A61M 5/1408* (2013.01);
    (Continued)

(58) Field of Classification Search
    CPC .............. A61M 5/007; A61M 5/16827; A61M 5/1408; A61M 5/1452; A61M 5/142;
    (Continued)

(56) References Cited

U.S. PATENT DOCUMENTS 5,840,026 A    11/1998   Uber, III et al.
5,882,338 A    3/1999    Gray
(Continued)

FOREIGN PATENT DOCUMENTS

EP      0255681 A2    2/1988
JP      4417621 B2    2/2010
(Continued)

OTHER PUBLICATIONS

Bae; Kyongtae, "Intravenous Contrast Medium Administration and Scan Timing at CT: Considerations and Approaches", Radiology, Jul. 2010, vol. 256: No. 1, pp. 32-61.

(Continued)

*Primary Examiner* — Peter Luong
(74) *Attorney, Agent, or Firm* — James R. Stevenson; Bryan P. Clark

(57) ABSTRACT

Provided is a method for delivering a medical fluid. The method includes delivering a fluid volume, which includes contrast and/or a flush fluid, at a preselected total volumetric flowrate during a first duration of a fluid delivery procedure. The amount of the contrast agent and the flush fluid in the fluid volume can be controllably varied during the first duration of the fluid delivery procedure so as to substantially maintain a preselected total volumetric flowrate throughout the first duration of the fluid delivery procedure. Also provided is a fluid delivery system capable of performing this method.

15 Claims, 9 Drawing Sheets

Related U.S. Application Data

(60) Provisional application No. 62/425,312, filed on Nov. 22, 2016.

(51) Int. Cl.
    *A61M 5/14*         (2006.01)
    *A61M 5/145*       (2006.01)
    *A61M 5/142*       (2006.01)

(52) U.S. Cl.
    CPC ... *A61M 5/1452* (2013.01); *A61M 2005/1403* (2013.01); *A61M 2005/14208* (2013.01); *A61M 2205/505* (2013.01)

(58) Field of Classification Search
    CPC .......... A61M 2005/1403; A61M 2005/14208; A61M 2205/505
    See application file for complete search history.

(56) References Cited

U.S. PATENT DOCUMENTS

| | | | |
|---|---|---|---|
| 6,055,985 | A | 5/2000 | Bae et al. |
| 6,385,483 | B1 | 5/2002 | Uber, III et al. |
| 6,635,030 | B1 | 10/2003 | Bae et al. |
| 6,643,537 | B1 | 11/2003 | Zatezalo et al. |
| 6,743,202 | B2 | 6/2004 | Hirschman et al. |
| 7,094,216 | B2 | 8/2006 | Trombley, III et al. |
| 7,556,619 | B2 | 7/2009 | Spohn et al. |
| 7,925,330 | B2 | 4/2011 | Kalafut et al. |
| 8,147,464 | B2 | 4/2012 | Spohn et al. |
| 8,295,914 | B2 | 10/2012 | Kalafut et al. |
| 8,337,456 | B2 | 12/2012 | Schriver et al. |
| 8,540,698 | B2 | 9/2013 | Spohn et al. |
| 9,008,759 | B2 | 4/2015 | Kalafut et al. |
| 9,302,044 | B2 | 4/2016 | Kalafut et al. |
| 9,421,330 | B2 | 8/2016 | Kalafut et al. |
| 9,616,166 | B2 | 4/2017 | Kalafut et al. |
| 9,750,953 | B2 | 9/2017 | Kalafut |
| 9,949,704 | B2 | 4/2018 | Kalafut et al. |
| 9,959,389 | B2 | 5/2018 | Kalafut |
| 10,016,618 | B2 | 7/2018 | Hirschman et al. |
| 2009/0234226 | A1 | 9/2009 | Nemoto |
| 2010/0030073 | A1 | 2/2010 | Kalafut et al. |
| 2011/0137160 | A1 | 6/2011 | Fago et al. |
| 2013/0041257 | A1 | 2/2013 | Nemoto |
| 2014/0261713 | A1 | 9/2014 | Schriver et al. |

FOREIGN PATENT DOCUMENTS

| | | |
|---|---|---|
| JP | 5203971 B2 | 6/2013 |
| WO | 2006055813 A2 | 5/2006 |
| WO | 2006058280 A2 | 6/2006 |
| WO | 2009012023 A1 | 1/2009 |
| WO | 2011163578 A2 | 12/2011 |

OTHER PUBLICATIONS

Bae, et al. "Aortic and Hepatic Contrast Medium Enhancement at CT—Part I, Prediction with a Computer Model", Radiology 1998;207:647-655.

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).

"International Preliminary Report on Patentability from PCT Application No. PCT/US2017/062728", dated Jun. 6, 2019.

Sahbaee Pooyan; et al, "The Effect of Contrast Material on Radiation Dose at CT: Part I—Incorporation of Contrast Material Dynamics in Anthropomorphic Phantoms", Radiology, 2017, pp. 1-10.

Schwilden, H., "A General Method for Calculating the Dosage Scheme in Linear Pharmacokinetics," European Journal of Clinical Pharmacology, vol. 20, pp. 379-386, 1981.

| | Length (cm) | Diameter (cm) | Area (cm^2) | Distended Volume (ml) | Velocity (cm/S) when at full area | Blood Flow (ml/S) | | Bae |
|---|---|---|---|---|---|---|---|---|
| Cephalic | 38 | 0.6 | 0.28 | 10.74 | | | Whole Arm at Rest 5.83+/-.67 | Whole arm 2.7 ml/S |
| Basilic | 24 | 0.8 | 0.50 | 12.06 | | | | |
| Brachial | | | | | | | | |
| Axillary | 13 | 1.6 | 2.01 | 26.14 | 1.34 | | | |
| Subclavian | 6 | 1.9 | 2.84 | 17.01 | | | | |
| right side from head | | | | | | | | 8.13 |
| R. Innominate | 2.5 | 1.9 | 2.84 | 7.09 | | | | |
| SVC | 7 | 2 | 3.14 | 21.99 | 6.90 | | | 21.67 |
| Heart | | | | | | | | 108.33 |

SYSTEM AND METHOD FOR DELIVERING A FLUID WITH A CONSISTENT TOTAL VOLUMETRIC FLOWRATE

CROSS REFERENCE TO RELATED APPLICATIONS

This application is a divisional of U.S. application Ser. No. 16/346,219 filed Apr. 30, 2019, which is a § 371 national stage application of International Patent Application No. PCT/US2017/062728, filed on Nov. 21, 2017, which claims the benefit of U.S. Provisional Patent Application Ser. No. 62/425,312, filed Nov. 22, 2016, the entire contents of which are hereby incorporated herein by reference. This application is related to International Patent Application No. PCT/US2017/062768, filed Nov. 21, 2017, which claims the benefit of U.S. Provisional Application Ser. No. 62/425,303, filed Nov. 22, 2016, the entire disclosure of which is hereby incorporated herein by reference.

BACKGROUND OF THE INVENTION

Field of the Invention

This disclosure is related to systems and methods for fluid delivery, and, particularly, to systems and methods for delivery of a fluid to a patient, such as delivery of a contrast agent to a patient during a medical injection and/or imaging procedure.

Description of Related Art

The following information is provided to assist the reader to understand the invention disclosed herein and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

It is often desirable to use a contrast agent to enhance images of a region of the body obtained through imaging procedures performed with scanning technologies such as, for example, computed tomography (CT), angiography, ultrasound, magnetic resonance imaging (MRI), nuclear medicine, and molecular imaging. Typically, the contrast agent is injected into a blood vessel of a patient and, once it flows to and reaches a desired concentration in the region of interest (ROI), the region is scanned by the scanner according to the imaging procedure selected by the radiologist or other medical personnel. The resulting contrast-enhanced images of the ROI can then be viewed on a display associated with the scanner itself or with another system such as a picture archiving and communication system (PACS) for purposes of reaching a diagnosis for and/or providing treatment to the patient.

In some cases, to reduce the amount of contrast used, the contrast agent injection is immediately followed by an injection of a flush fluid, such as saline. This is commonly done to improve the efficiency of the use of contrast agent, either to save money or to reduce the effect of the contrast agent on the patient's body or both. This saline injection helps to flush or wash the contrast agent out of the peripheral veins and into the central circulation. This also helps reduce the creation of artifacts that may be created by concentrated contrast agent in the arms being in the CT beam. A saline flush has been found especially useful when small volumes of contrast agent are used, as in MRI.

In certain imaging procedures, it is also desirable to produce different levels of enhancement in two or more regions of the body or in different tissues in the same region of the body. For example, in various cardiac imaging procedures, it is desirable to produce high contrast in the coronary arteries and at the same time moderate contrast in the right heart so that both the diameters of the arterial lumens and the motion of the heart wall can be visualized in one scan without artifacts caused by, for example, concentrated contrast streaming into the right heart.

To achieve this with an injection system with a single concentration of contrast and no saline flush capability, a first phase with a high contrast delivery rate is initially injected (a given concentration at a high flowrate). The second or following phase has a reduced contrast delivery rate (same concentration at a reduced flowrate). If the injection system has a saline flush capability, there may be a third phase with a saline flush at the volumetric flowrate of either the first or the second phase.

It is not generally realized that in injection procedures in which the flow of the contrast is slowed down in the second phase (in this case with no saline), the flow of the fluid that has already been injected and is downstream of the intravenous (IV) catheter tip also slows down because the flow in the veins is the sum of the native or natural flowrate and the injected flowrate. This causes the shape of the contrast bolus to change downstream of the injection site and thus as it arrives in the heart. For example, FIG. 7 provides example details on anatomical variations in the circulatory system of the human body inclusive of the exemplary changes in the diameter of vessels in the human body as they lead to and approach the human heart. FIG. 8 provides a rudimentary model of the flow of fluid through the venous system, illustrating how the larger "pipes" closer to the heart accommodate increased flow. While an injected fluid flow added to the existing flow may be high enough to significantly change the flow in some vessels, it may not be enough to significantly change the flow in other vessels. As flow rate decreases, the flow downstream changes nearly instantaneously, but nonlinearly due in part to the fact that the venous system is comprised of "pipes" that can stretch or change volume depending on the magnitude of the flow. Consequently, in this prior art injection method, this changes the concentration of contrast in the blood at that location, and it also reduces the quality and consistency of the images taken of that ROI as they are now dependent upon the native flow in the patient's vessels and the vessel geometry.

In the OptiBolus™ Bolus Shaping Software offered by the Guerbet Group (formerly by Mallinckrodt), the method of contrast administration involves an injection procedure that employs a truncated, exponentially decaying bolus profile in the first phase with or without use of a saline flush. FIG. 2A, for example, shows a normal Optibolus profile in the first and only phase without the use of a saline flush. FIG. 3A, however, shows the OptiBolus profile in the first phase with the use of a saline flush in the second phase at the flowrate equal to that of the contrast at the end of the first or contrast phase. As discussed below, the OptiBolus profiles follow the models and injection protocols discussed in U.S. Pat. Nos. 6,055,985 and 6,635,030, both to Bae et al., the entire contents of each of which are incorporated herein by reference.

Similarly, in the approach developed by Fleischmann et al. (described in the article "Mathematical Analysis of Arterial Enhancement and Optimization of Bolus Geometry for CT Angiography Using the Discrete Fourier Transform," Journal of Computer Assisted Tomography, Volume 23(3), May/June 1999, pp. 474-484), they employ a method that attempts to determine an ideal bolus profile, as shown in FIG. 4A herein, using the response of the patient to a test bolus. Because of the limitations inherent to injection systems, however, Fleischmann et al. approximate that comparatively more complex ideal bolus profile with the "normal bolus profile" shown in FIG. 5A herein. This normal profile is manifested as a relatively large magnitude rectangular bolus of contrast in the first phase of an injection procedure followed by a comparatively smaller, long rectangular contrast bolus in the second phase of the procedure.

In the Personalized Patient Protocol Technology (P3T®) software pioneered by Bayer, the method of administration employs a three-phase injection procedure as shown in FIG. 6. A large normal rectangular contrast bolus is carried out in the first phase followed by a second phase, a phase of dual fluid flows, composed of a mix of contrast and saline injected at the same total flow rate used in the first phase. This is followed by an all saline bolus in the third phase, again at the same total flow rate to avoid the problem of the bolus being adversely affected downstream by a change in the injected flow rate. In each of the above referenced figures, the volume of contrast delivered is represented by the area "C" while the volume of flush fluid (e.g., saline) delivered is represented by the area "F."

Dual flow injection protocols involve the administration of different contrast concentrations at a reasonably consistent total volumetric flowrate. This may be achieved by injecting contrast and/or saline in varying ratios into a patient over the course of one or more phases of injection. For example, in a typical dual flow injection procedure, as shown in FIG. 6, a contrast medium at full strength is injected during a first phase of the procedure, an admixture of both contrast and saline is injected during a second phase, and then a third phase may be employed in which only saline is injected as a means to push the injected fluid as a bolus through the vasculature to the region(s) of interest. In the context of cardiac imaging, the reason multi-phase dual flow injections are used is to at least mitigate the left heart/right heart imaging issue. To do so, it is important that the injection procedure will consistently result in the formation of a bolus that will enable the arrival and presence of contrast, in the appropriate concentration and amount, in the desired vessel/ROIs at the same time that the vessel/ROIs is/are being scanned so as to produce contrast-enhanced images of the highest possible resolution throughout the entirety of the ROI.

SUMMARY

An object of certain embodiments of this disclosure is to bring the benefits of a consistent total volumetric flow rate to the situation of delivering complex, continuously varying, or optimized bolus shapes. The more complicated the bolus profile, the more important it is to have a consistent total volumetric flow rate to preserve the desired shape of the bolus into the central circulation.

As will become apparent in the following paragraphs, the embodiments described herein can be applied to a variety of prior art bolus delivery or optimization techniques including those attempted by, for example, Mallinckrodt/Guerbet/Bae and Fleischmann et al. The provision of a consistent volumetric flow rate over the delivery of the contrast and flushing fluid enables the bolus shape in the vessels and/or tissue of interest to be closer to what is expected or predicted and less dependent on patient to patient variation as well as variations for the same patient over time. This enables better scan timing and more consistent image quality. By reducing variation, it may be possible to reduce radiation and/or contrast media volumes as well.

In some non-limiting aspects of this disclosure, provided is a method for delivering a medical fluid. The method includes delivering a fluid volume at a preselected total volumetric flowrate during a first duration of a fluid delivery procedure, wherein the fluid volume is comprised of a volumetric amount of a contrast agent and, optionally, a volumetric amount of a flush fluid. The method also includes controllably varying the volumetric amount of the contrast agent in the fluid volume during the first duration of the fluid delivery procedure and controllably varying the volumetric amount of the flush fluid in the fluid volume during the first duration of the fluid delivery procedure so as to substantially maintain the preselected total volumetric flowrate throughout the first duration of the fluid delivery procedure.

In other non-limiting aspects of this disclosure, provided is a fluid delivery system. The system includes a fluid administration device adapted to deliver a fluid volume, wherein the fluid volume comprises a volumetric amount of a contrast agent and, optionally, a volumetric amount of a flush fluid. The system also includes a controller in communication with the fluid administration device, wherein the controller comprises a processor and a non-transitory machine-readable storage medium. The non-transitory machine-readable storage medium comprises instructions that, when executed by the processor, enable the fluid administration device to: deliver the fluid volume at a preselected total volumetric flowrate during a first duration of a fluid delivery procedure; controllably vary the volumetric amount of the contrast agent in the fluid volume during the first duration of the fluid delivery procedure; and controllably vary the volumetric amount of the flush fluid in the fluid volume during the first duration so as to substantially maintain the preselected total volumetric flowrate throughout the first duration of the fluid delivery procedure.

Various aspects of the present disclosure may be further characterized by one or more of the following clauses:

Clause 1. A method for delivering a medical fluid, comprising: delivering a fluid volume at a preselected total volumetric flowrate during a first duration of a fluid delivery procedure, wherein the fluid volume is comprised of a volumetric amount of a contrast agent and, optionally, a volumetric amount of a flush fluid; controllably varying the volumetric amount of the contrast agent in the fluid volume during the first duration of the fluid delivery procedure; and controllably varying the volumetric amount of the flush fluid in the fluid volume during the first duration of the fluid delivery procedure so as to substantially maintain the preselected total volumetric flowrate throughout the first duration of the fluid delivery procedure.

Clause 2. The method of clause 1, wherein the volumetric amount of the contrast agent in the fluid volume is controllably decreased during the first duration of the fluid delivery procedure.

Clause 3. The method of either of clauses 1 or 2, wherein the volumetric amount of the flush fluid in the fluid volume is controllably increased during the first duration of the fluid delivery procedure.

Clause 4. The method of any of clauses 1-3, wherein the volumetric amount of the contrast agent in the fluid volume is continuously decreased during the first duration of the fluid delivery procedure.

Clause 5. The method of any of clauses 1-4, wherein the volumetric amount of the flush fluid in the fluid volume is continuously increased during the first duration of the fluid delivery procedure.

Clause 6. The method of any of clauses 1-5, wherein the volumetric amount of the contrast agent in the fluid volume is both controllably decreased and controllably increased during the first duration of the fluid delivery procedure.

Clause 7. The method of any of clauses 1-6, wherein the volumetric amount of the flush fluid in the fluid volume is both controllably increased and controllably decreased during the first duration of the fluid delivery procedure.

Clause 8. The method of any of clauses 1-7, wherein the delivery of the contrast agent is substantially completed during the first duration.

Clause 9. The method of any of clauses 1-8, wherein the volumetric amount of the contrast agent in the fluid volume is greater than zero during the first duration of the fluid delivery procedure Clause 10. The method of any of clauses 1-9, further comprising: delivering a second fluid volume at a second preselected total volumetric flowrate during a second duration of the fluid delivery procedure, which is after the first duration, wherein the second fluid volume is comprised of a second volumetric amount of the flush fluid and, optionally, a second volumetric amount of the contrast agent; and maintaining the second preselected total volumetric flowrate throughout the second duration of the fluid delivery procedure.

Clause 11. The method of clause 10, wherein the second preselected total volumetric flowrate is substantially the same as the first preselected total volumetric flowrate.

Clause 12. The method of either of clauses 10 or 11, wherein the second fluid volume consists entirely of the flush fluid.

Clause 13. The method of any of clauses 10-12, wherein the second duration of the fluid delivery procedure immediately follows the first duration of the fluid delivery procedure.

Clause 14. The method of any of clauses 10-13, wherein the fluid delivery procedure is substantially completed during the second duration.

Clause 15. The method any of clauses 1-9, further comprising: delivering a second fluid volume at a second preselected total volumetric flowrate during a second duration, which is after the first duration, of the fluid delivery procedure, wherein the second fluid volume is comprised of a second volumetric amount of the contrast agent and, optionally, a second volumetric amount of the flush fluid; controllably varying the second volumetric amount of the contrast agent in the second fluid volume during the second duration of the fluid delivery procedure; and controllably varying the second volumetric amount of the flush fluid in the second fluid volume during the second duration of the fluid delivery procedure so as to substantially maintain the second preselected total volumetric flowrate throughout the second duration of the fluid delivery procedure.

Clause 16. The method of clause 15, wherein the second preselected total volumetric flowrate is substantially the same as the first preselected total volumetric flowrate.

Clause 17. The method of either of clauses 15 or 16, wherein the second duration of the fluid delivery procedure immediately follows the first duration of the fluid delivery procedure.

Clause 18. A fluid delivery system, comprising: a fluid administration device adapted to deliver a fluid volume, wherein the fluid volume comprises a volumetric amount of a contrast agent and, optionally, a volumetric amount of a flush fluid; and a controller in communication with the fluid administration device, wherein the controller comprises a processor and a non-transitory machine-readable storage medium, wherein the non-transitory machine-readable storage medium comprises instructions that, when executed by the processor, enable the fluid administration device to: deliver the fluid volume at a preselected total volumetric flowrate during a first duration of a fluid delivery procedure; controllably vary the volumetric amount of the contrast agent in the fluid volume during the first duration of the fluid delivery procedure; and controllably vary the volumetric amount of the flush fluid in the fluid volume during the first duration so as to substantially maintain the preselected total volumetric flowrate throughout the first duration of the fluid delivery procedure.

Clause 19. The fluid delivery system of clause 18, further comprising a source of the contrast agent and a source of the flush fluid.

DETAILED DESCRIPTION

Figure 1:
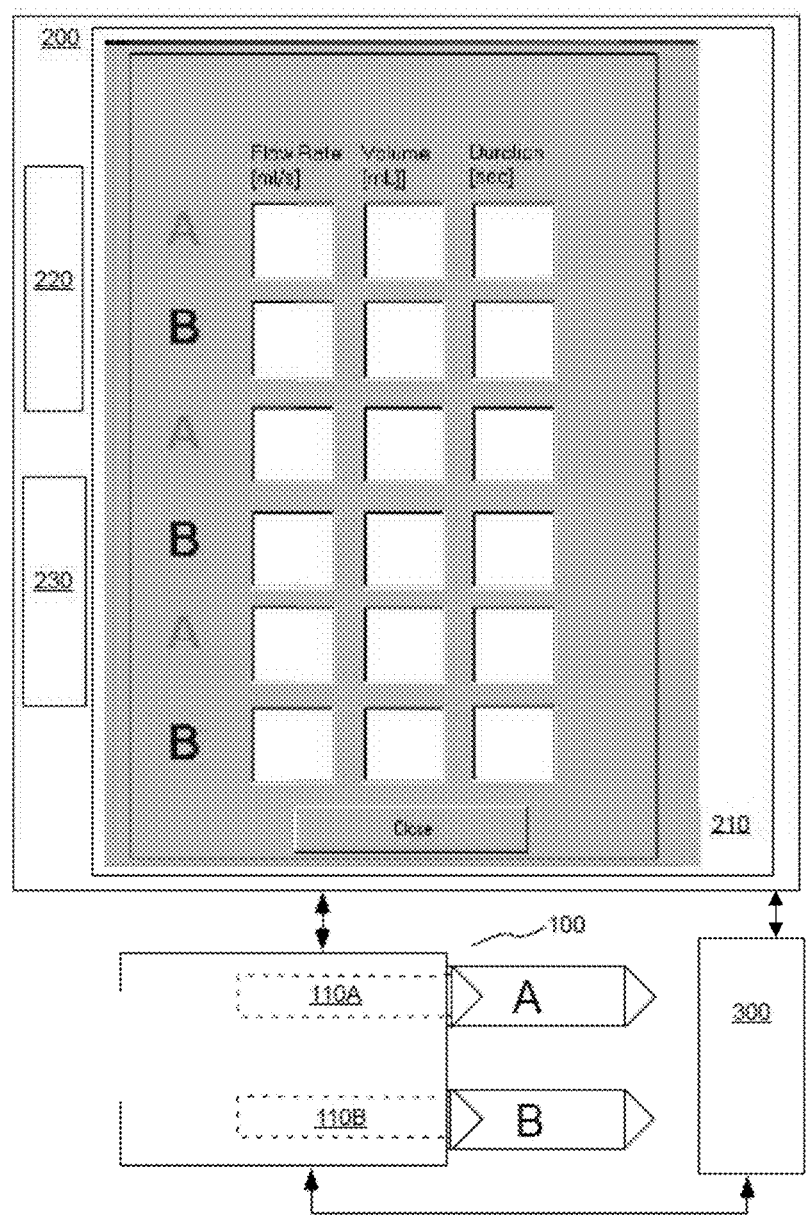
FIG. 1 illustrates an embodiment of a Graphical User Interface (GUI) to set forth parameters for a plurality of phases for a two-syringe injector also illustrated in FIG. 1.

For purposes of the description hereinafter, spatial orientation terms shall relate to the embodiment as it is oriented in the drawing figures. However, it is to be understood that the various embodiments of this disclosure may assume alternative variations and step sequences, except where expressly specified to the contrary. It is also to be understood that the specific devices and processes illustrated in the attached drawings, and described in the following specification, are simply exemplary. Hence, specific dimensions and other physical characteristics related to the embodiments disclosed herein are not to be considered as limiting.

As used in the specification, the singular form of "a", "an", and "the" include plural referents unless the context clearly dictates otherwise.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

All documents, such as but not limited to issued patents and patent applications, referred to herein, and unless otherwise indicated, are to be considered to be "incorporated by reference" in their entirety.

According to one aspect of this disclosure, a method for delivering a medical fluid is described. The medical fluid can include, but is not limited to, a contrast agent, a flush fluid, and combinations thereof. The delivery of medical fluid can be part of an injection procedure in which the medical fluid is delivered to a patient, though this disclosure is not limited to fluid delivery only for this purpose.

The medical fluid can be delivered according to a "protocol." As used herein with respect to a fluid delivery procedure, the term "protocol" refers to a group of parameters such as flow rate, flow volume, delivery duration, etc. that define the amount of fluid(s) to be delivered during a fluid delivery procedure, such as to a patient during an injection procedure. Such parameters can change over the course of the procedure. As used herein, the term "phase" refers generally to a group of parameters that define the amount of fluid(s) to be delivered during a period of time (or phase duration) that can be less than the total duration of the fluid delivery procedure. The term "duration" is used to refer to any period of time of the fluid delivery procedure. A "duration" may be, in some instances, equivalent to a phase or to the entire delivery procedure, though it may also be used to refer to a more limited period of time. Thus, the parameters of a phase or a duration provide a description of the fluid delivery over a time instance corresponding to the length of time of the phase or the duration. By way of example, one parameter can be the initial total volumetric flow rate, which corresponds to the total volume of fluid per unit time being delivered at the onset of the phase. This initial total volumetric flowrate may be comprised of the fluid volume of more than one fluid, such as a first fluid and second fluid, that are being delivered simultaneously. For example, if, at the onset of a phase, a flowrate of a first fluid is 5 mL/s and a flowrate of a second fluid is 2 mL/s, the initial total volumetric flowrate would be 7 mL/s. Similarly, if the fluid delivery protocol requires only the first fluid to be delivered at the onset of the phase, again at a flow rate of 5 mL/s, while none of the second fluid is delivered at the onset of the phase, the initial total volumetric flowrate would be 5 mL/s.

A fluid delivery protocol for a particular procedure can, for example, be described as uniphasic (a single phase), biphasic (two phases), or multiphasic (two or more phases, but typically more than two phases). Multiphasic procedures also include procedures in which the parameters, such as flowrate, can change or vary continuously, semi-continuously, discretely, or in multiple steps over at least a portion of the procedure. A continuously varying flowrate can be achieved through many approaches, including curvilinear approximations, piecewise linear approximations, or a stepwise approximation.

As mentioned, the delivery of medical fluid described herein can be part of an injection procedure in which the medical fluid is delivered to a patient. An injection system 100 illustrated in FIG. 1 can be used with the present disclosure. System 100 includes two fluid delivery sources (sometimes referred to as source "A" and source "B" herein; such as syringes) that are operable to introduce a first fluid and/or a second fluid (for example, contrast agent, saline, etc.) to the patient independently (for example, simultaneously, simultaneously in different volumetric flow proportion to each other, or sequentially or subsequent to each other (that is, A then B, or B then A)). Exemplary injection systems are those that are disclosed in: U.S. patent application Ser. No. 09/715,330, filed on Nov. 17, 2000, issued as U.S. Pat. No. 6,643,537; U.S. patent application Ser. No. 09/982,518, filed on Oct. 18, 2001, issued as U.S. Pat. No. 7,094,216; U.S. patent application Ser. No. 10/825,866, filed on Apr. 16, 2004, issued as U.S. Pat. No. 7,556,619; U.S. patent application Ser. No. 12/437,011, filed May 7, 2009, issued as U.S. Pat. No. 8,337,456; U.S. patent application Ser. No. 12/476,513, filed Jun. 2, 2009, issued as U.S. Pat. No. 8,147,464; and U.S. patent application Ser. No. 11/004,670, filed on Dec. 3, 2004, issued as U.S. Pat. No. 8,540,698, the disclosures of each of which are incorporated herein by reference in their entireties.

In the embodiment of FIG. 1, source A is in operative connection with a pressurizing mechanism such as a drive member 110A, and source B is in operative connection with a pressurizing mechanism such as a drive member 110B. Injection system 100 includes a controller 200 in operative connection with injector system 100 that is operable to control the operation of drive members 110A and 110B to control injection of fluid A (for example, a contrast agent) from source A and injection of fluid B (for example, a flush fluid such as saline) from source B, respectively. Controller 200 can, for example, include a user interface comprising a display 210. Controller 200 can also include a processor 220 (for example, a digital microprocessor as known in the art) in operative connection with a memory 230. The memory 230 can be a non-transitory machine-readable storage medium that includes program instructions that can be executed by the processor 220 to allow controller 200 to control the injection system 100 so as to perform the processes discussed herein, among other functions. Imaging system 300 can, for example, be a CT system, a MRI system, an ultrasound imaging system, a positron emission tomography (PET) system or another imaging system. Injection system 100 can be in communicative connection with imaging system 300 and one, a plurality, or all the components of injection system 100 and imaging system 300 can be integrated.

In some non-limiting embodiments, system 100 may include a single computer, a server computer, a combination of computers, or any other combination of hardware and/or software components. Controller 200 may be considered to be an integral aspect of the injector 100 or a separate but connected aspect of the overall imaging system 100. The individual units or components of system 100 may be localized or, in some embodiments, distributed among any number of hardware devices, local or remote, preferably in communication with one another. Further, each unit may itself be comprised of a distributed system, such as a series of servers and/or computers networked together. In one non-limiting example, certain components of system 100 may be incorporated into the software and hardware associated with medical imaging equipment (e.g., scanner and injector), such as the Certegra® Workstation product offered by Bayer HealthCare LLC.

In several embodiments of the present disclosure, phase variables or parameters are populated within a phase programming mechanism (see FIG. 1 for an embodiment of a user interface therefor that can, for example, be used with injector system 100) based on one or more parameters of interest, including, for example, but not limited to, contrast agent concentration (for example, iodine concentration in the case of a CT procedure), a patient parameter (for example, body weight, body mass index (BMI), height, gender, age, cardiac output, etc.) the type of scan being performed, and the type of catheter inserted into the patient for intravascular access. As discussed above, differences in dosing requirements for different patients during imaging and other procedures have been recognized. For example, U.S. Pat. Nos. 5,840,026 and 6,385,483, assigned to the assignee of the present invention, the disclosures of which are incorporated herein by reference, disclose devices and methods to customize the injection to the patient using patient specific data derived before or during an injection. Likewise, U.S. Pat. No. 8,295,914, assigned to the assignee of the present invention, the disclosure of which is incorporated herein by reference, also discloses customization of injections to a patient using patient specific data and sets forth a number of models to describe a time enhancement output for a given input or protocol.

The clinical operator can control the injection system 100 either by entering volumes and flowrates manually into the fields provided on the user interface, by selecting a predefined protocol, or by using software associated with the system, such as software in the form of programming instructions residing in the non-transitory computer readable medium of memory 230, to compute a protocol. The software associated with the system 100 may compute an injection protocol for the delivery of a fluid volume over time where the fluid volume includes at least a volumetric amount of a first fluid, such as contrast agent, delivered at a flowrate that may vary over time and may be zero at certain times, and a volumetric amount of a second fluid, such as saline, which also may be delivered at a flowrate that may vary over time and may be zero at certain times.

The injection protocol can be determined by first determining the parameters (e.g., total volume, flowrate over time, etc.) for delivering the contrast agent, which collectively make up a contrast agent protocol. The software can follow, for example, any of a variety of known models for determining the contrast agent protocol. These include, but are not limited to, contrast agent protocols that have been developed to achieve a desired bolus profile or shape.

In one non-limiting embodiment, the delivery of contrast agent can follow one of the contrast agent protocols described in U.S. Pat. Nos. 6,055,985 and 6,635,030, both to Bae et al., the entire contents of each of which are incorporated herein by reference. Bae et al. describe a methodology for determining a protocol for delivering a contrast agent to a patient which attempts to optimize the use of contrast agent to achieve an enhancement in excess of a preselected threshold and to maintain that excess level of enhancement for a temporal duration that is near optimal given the amount of contrast used.

For example, in U.S. Pat. No. 6,055,985, Bae et al. set forth various ramped, or multiphasic, or exponentially decaying, or steadily decreasing injection rates. Bae et al. solve a set of differential equations describing a simplified compartment model of a patient's body to render an exponentially decaying rate of contrast injection having a particular decay coefficient, though it was contemplated that in the real world, this exponentially decaying injection rate could be approximated by a linear decay, or ramped decay, or even a multi-step decay. The particular decay coefficient calculated by Bae et al. is proportional to the cardiac output per body weight of the patient and is approximated to be 0.01.

In one non-limiting embodiment of Bae et al., the contrast agent protocol is determined by an initial delivery rate and an exponential decay coefficient. This is illustrated in FIG. 3 of U.S. Pat. No. 6,055,985, a representation of which is provided as FIG. 2A herein. The initial delivery rate can be, for example, 2 mL/s. The total injected volume of contrast agent corresponds to the integrated sum of the injection over the injection duration. The total injected volume of contrast agent can be, for example, 50 mL, 70 mL, or 90 mL. Bae et al. also disclose an exponential decay coefficient equal to Q/Vs, which is the ratio of cardiac output (Q) to the systematic volume of distinction of contrast agent, which itself is proportional to the cardiac output per body weight (Vs). Bae et al. disclose and focus on decay coefficients at or near 0.01, 0.02, and 0.03 and an injection duration of 120 seconds.

Bae et al. propose a contrast injection routine where an interval of the routine begins at a preselected initial flowrate of contrast agent and then the flowrate is controllably decreased during the routine at substantially an exponential rate having a decay coefficient that approximates the cardiac output per body weight that is typical of the patient. Bae et al. also teach that functional patterns other than an exponential decay may be used to deliver the contrast agent, including approximating a short segment of an exponential curve by a linear or ramped contrast agent protocol. Bae et al. provide an exemplary contrast agent protocol in which delivery of a contrast agent begins at a preselected initial injection flowrate and then the flowrate is controllably and continuously decreased, such as along a path of exponential decay, until the desired volume of contrast has been delivered and/or the desired injection duration has elapsed.

The techniques described by Bae et al. can be applied to the present disclosure as a method of delivering a volumetric amount of a contrast agent by controllably varying the flowrate of the contrast agent during a least a portion of the injection procedure. For example, a contrast agent protocol for a particular patient can be determined according to the techniques set forth by Bae et al. This contrast agent protocol can form part of the injection protocol, and particularly the portion of the injection protocol that controls the delivery of a contrast agent.

In another non-limiting embodiment, the delivery of contrast agent can follow one of the contrast agent protocols described in the article "Mathematical Analysis of Arterial Enhancement and Optimization of Bolus Geometry for CT Angiography Using the Discrete Fourier Transform," Journal of Computer Assisted Tomography, Volume 23(3), May/June 1999, pp. 474-484, by Fleischmann et al., the entire contents of which are incorporated by reference.

Fleischmann et al. describe a mathematical technique for the analysis of an individual patient's contribution, referred to therein as the "patient function," to the patient's time-attenuation response to intravenously injected contrast material. Fleischmann et al. assert that their technique can be used to predict the time-attenuation response to a given contrast agent bolus injection and calculate individually "optimized" injection parameters, which aim to achieve a uniform arterial opacification at a pre-defined level of enhancement for the entire scanning.

According to Fleischmann et al., a small bolus injection, a test bolus injection, of contrast agent (16 ml of contrast at 4 ml/s) is made prior to a diagnostic scan. A dynamic enhancement scan is then made across a vessel of interest. The resulting processed scan data (test scan) is interpreted as the impulse response of the patient/contrast agent system. Fleischmann et al. derived the Fourier transform of the patient transfer function by dividing the Fourier transform of the test scan by the Fourier transform of the test injection. Assuming the system was a linear time invariant (LTI) system and that the desired output time domain signal was known (a flat diagnostic scan at a predefined enhancement level), Fleischmann et al. derived an input time signal by dividing the frequency domain representations of the desired output by that of the patient transfer function. Because the method of Fleischmann et. al. computes input signals that are not realizable in reality as a result of injection system limitations (for example, flow rate limitations), one must truncate and approximate the computed continuous time signal.

Fleischmann et al. also describe a technique to characterize, predict, and optimize enhancement using a set of mathematical relations. The relations can be assembled into a notebook file of a commercially available computer program (Mathematica for Windows, enhanced version 2.2.3; Wolfram Research, Champaign, Ill., U.S.A.). The Mathematica notebook requires the input of (a) the test bolus, (b) the corresponding test enhancement, (c) the parameters of an arbitrary standard bolus, and finally (d) the desired "ideal" arterial enhancement.

To predict enhancement and to calculate an optimized injection bolus for an individual, the following steps were implemented by Fleischmann et al. Step 1: from the parameters (volume, flow rate) of the test bolus and the corresponding arterial time-attenuation response, the program calculates the patient function in the Fourier space from the relation of a test bolus to a patient's corresponding aortic time-attenuation response, the test enhancement. The patient function plays the central role in predicting the individual enhancement response to a given bolus (e.g., a standard uniphasic injection), as well as in calculating the "ideal" injection parameters for a theoretically ideal (near rectangular) enhancement curve. Step 2: once the patient function is known, the standard enhancement to an arbitrary bolus, e.g., a 120 ml standard bolus, can be predicted. Step 3: with the use of the patient function, calculate a theoretically "ideal" bolus, which should achieve a near rectangular enhancement. Step 4: since the theoretically "ideal bolus" contains "unreal" components in the time domain, like oscillations, or negative flow rates, a fitting algorithm is introduced to approximate the ideal flow rates into a practically applicable optimized biphasic bolus. The corresponding optimized enhancement can be predicted as described in Step 2. Step 4 represents an independently developed fitting process in the time domain so as to produce a normal profile.

Figure 4A:
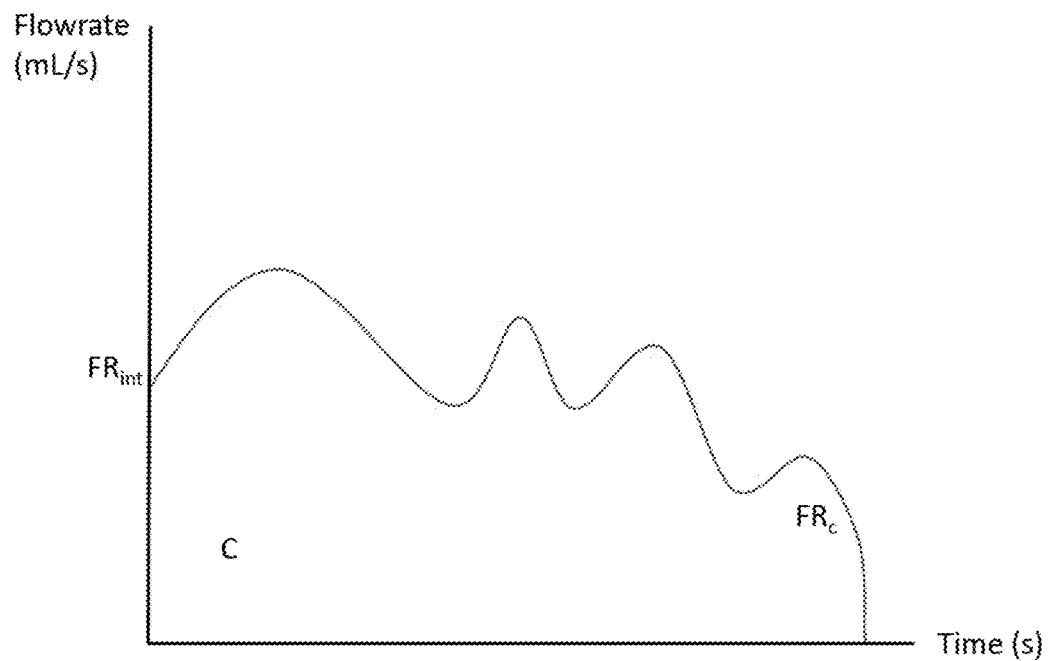
FIG. 4A is a graph of an injection profile of a contrast agent according to one embodiment of Fleischmann et al.
Figure 5A:
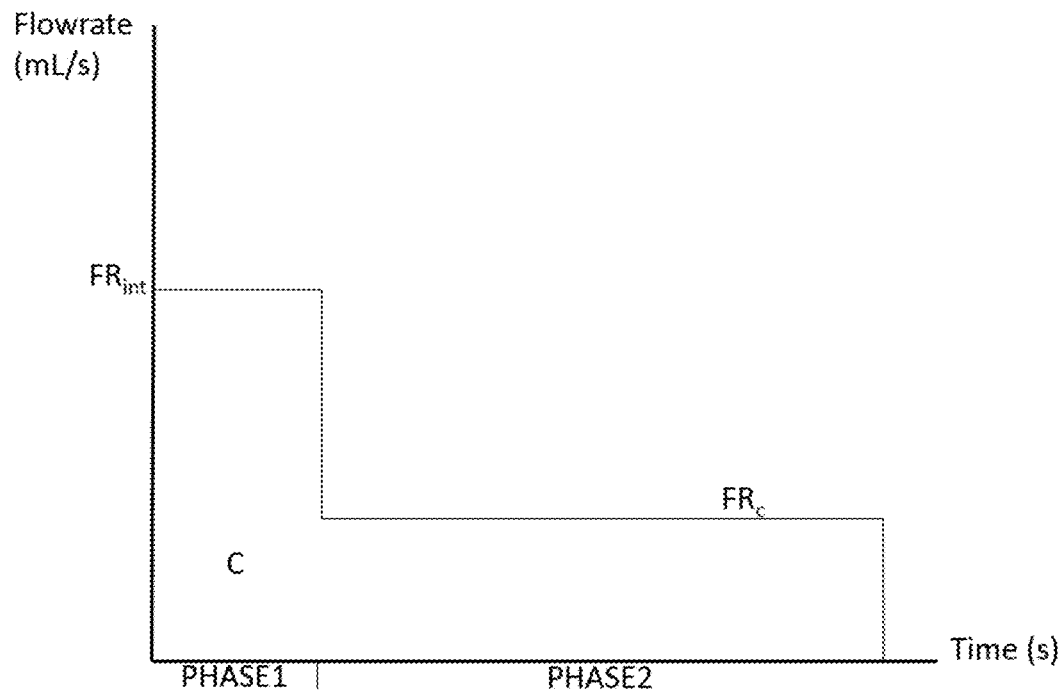
FIG. 5A is a graph of an injection profile of a contrast agent according to another embodiment of Fleischmann et al.

A representation of an ideal bolus profile calculated according to the methods described by Fleischmann et al. is shown in FIG. 4A while an approximation of this comparatively complex ideal bolus profile, referred to as a normal bolus profile, is shown in FIG. 5A. This normal profile is manifested as a relatively large magnitude rectangular bolus of contrast in the first phase of an injection procedure followed by a comparatively smaller, long rectangular contrast bolus in the second phase of the procedure.

The techniques described by Fleischmann et al. can be applied to the present disclosure as a method of delivering a volumetric amount of a contrast agent by controllably varying the flowrate of the contrast agent during a least a portion of the injection procedure. For example, a contrast agent protocol for a particular patient can be determined according to the process set forth by Fleischmann et al. This contrast agent protocol can form part of the injection protocol, and particularly the portion of the injection protocol that controls the delivery of a contrast agent.

The above described contrast agent protocols are intended to be exemplary only. One of skill in the art would recognize, upon reading the present disclosure, that a fluid delivery procedure may employ other contrast agent protocols, including other protocols in which the flowrate of contrast varies over time, such as contrast agent protocols in which the delivery of contrast continuously varies over the course of administering the contrast agent.

As mentioned, the fluid volume delivered according to an injection protocol of the present disclosure can include, in addition to a volumetric amount of a contrast agent, which can be delivered according to the contrast agent protocols discussed above, a volumetric amount of a flush fluid, such as saline. Like with the delivery of contrast, the volumetric amount of the flush fluid may be delivered at a flowrate that varies throughout the injection procedure.

In one aspect of this disclosure, the parameters for the delivery of the flush fluid are selected so as to substantially maintain a consistent total volumetric flowrate throughout at least some duration of the fluid delivery procedure. For example, a substantially consistent total volumetric flowrate can be maintained throughout the entirety of at least one phase of the fluid delivery procedure. By way of another example, a substantially consistent total volumetric flowrate can be maintained throughout at least that portion of the procedure where contrast agent is being delivered. In yet another example, a substantially consistent total volumetric flowrate can be maintained throughout the entirety of the fluid delivery procedure, such as across all phases of a multiphasic procedure.

The total volumetric flowrate value that is maintained can be a preselected value that is selected in advance of initiating the fluid delivery procedure or a phase thereof. In one non-limiting embodiment, the total volumetric flowrate that is maintained is substantially the same as the initial total volumetric flowrate at the onset of the fluid delivery procedure or a phase thereof. In another non-limiting embodiment, the total volumetric flowrate that is maintained is higher than the initial total volumetric flowrate at the onset of the fluid delivery procedure or a phase thereof. In this embodiment, the initial total volumetric flowrate is increased, such as through a gradual ramp up, so that the total flowrate reaches the preselected total volumetric flowrate. Use of this ramp up period can help avoid the whip or shock to a patient's venous system that could come through the sudden administration of a high fluid volume. In yet another non-limiting embodiment, the initial total volumetric flowrate at the onset of the fluid delivery procedure or a phase thereof is greater than the preselected total volumetric flowrate. The initial total volumetric flowrate is then decreased so that the total flowrate reaches the preselected total volumetric flowrate. In one non-limiting embodiment, the total volumetric flowrate that is maintained may be equal to the maximum flowrate of contrast agent achieved during the fluid delivery procedure. In another non-limiting embodiment, the total volumetric flowrate that is maintained may be greater than the maximum flowrate of contrast agent achieved during the fluid delivery procedure. Regardless of the relationship between the initial total volumetric flowrate and the preselected total volumetric flowrate that is maintained, the total volumetric flowrate can be gradually ramped down toward the end of the fluid delivery procedure or phase thereof to, for example, avoid pressure bleed off. The flow may dither, oscillate, or vary at a frequency high enough that it is smoothed out by the fluid vessel volume and flows in the body, effectively providing a sufficiently constant total volumetric flow.

Figure 7:
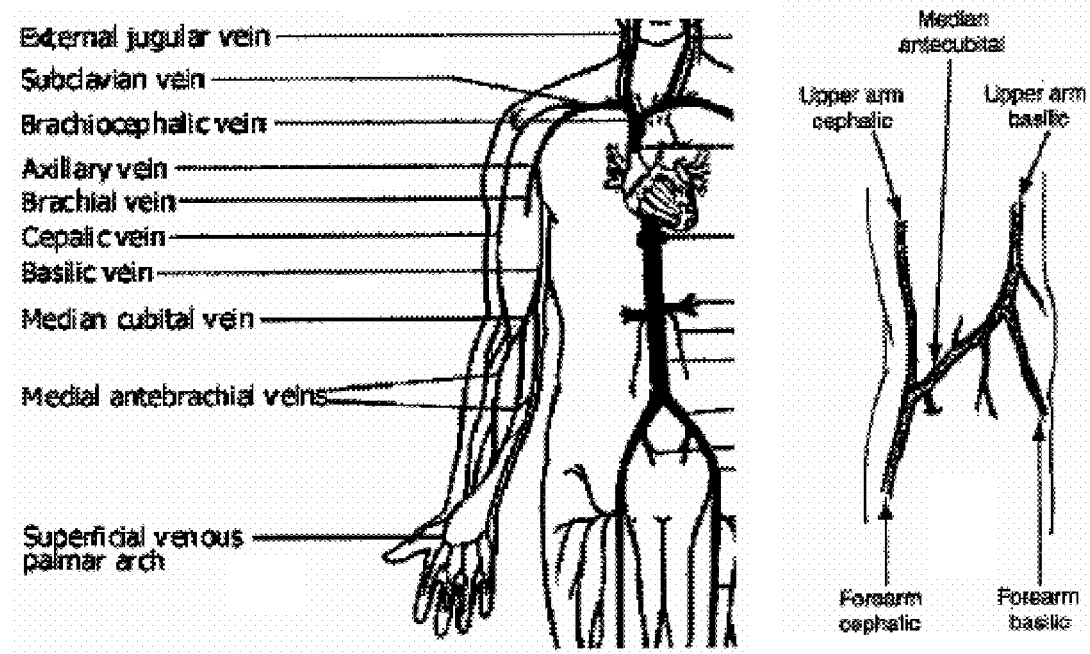
FIG. 7 is an illustration of the human body circulatory system and exemplary sizes of different portions thereof.
Figure 8:
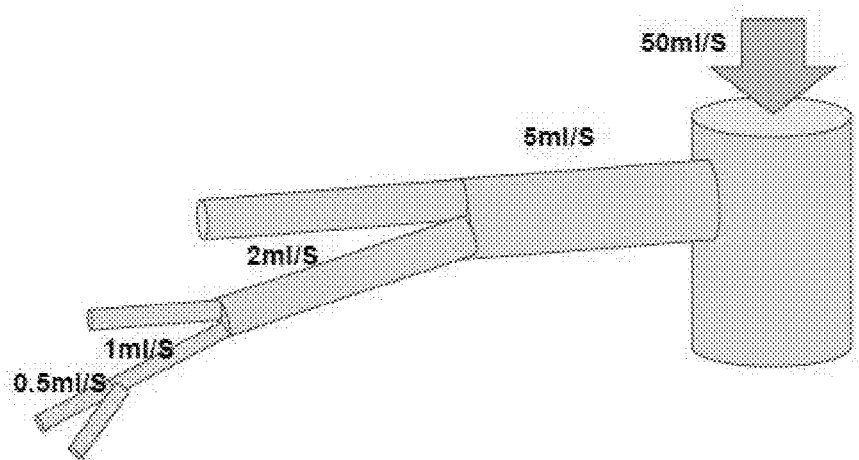
FIG. 8 is an illustration of a model of the venous system showing an example of how the flowrates in different portions thereof can vary.

For purposes of this disclosure, a "substantially consistent total volumetric flowrate" means that the fluid volume per unit time remains constant over the timeframes and intervening fluid volumes relevant to the contrast reaching the regions of interest within a target margin of variation over the timeframe of interest in the imaging study. An exemplary target may be a margin of variation of less than 20% by volume, such as less than 10% or less than 5% by volume. The specific numeric value may depend upon the injection flow rate in relation to the patient's peripheral vessel flowrates as discussed above in relation to FIGS. 7 and 8. As discussed above, the fluid volume can include more than one fluid. For example, the fluid volume can include a volumetric amount of a contrast agent and a volumetric amount of a flush fluid such as saline. Two contrasts of different concentrations may be used. Alternatively, three or more fluids may be used, for example two contrasts with properties that may be distinguished by the imaging system in use and a flush fluid such as saline.

Figure 2A:
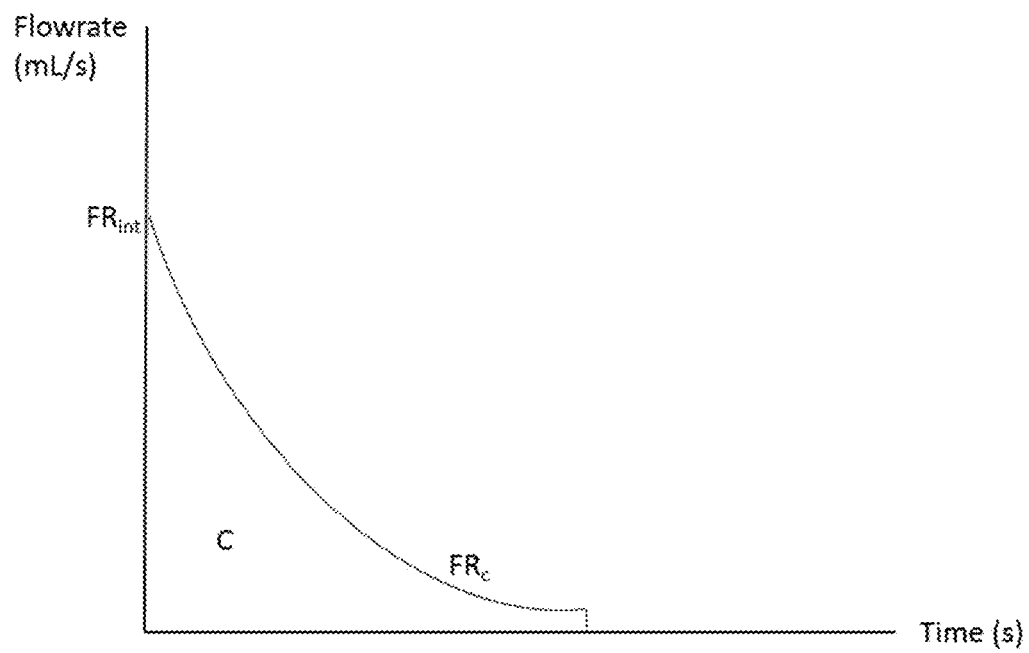
FIG. 2A is a graph of an injection profile of a contrast agent according to one embodiment of Bae et al.
Figure 2B:
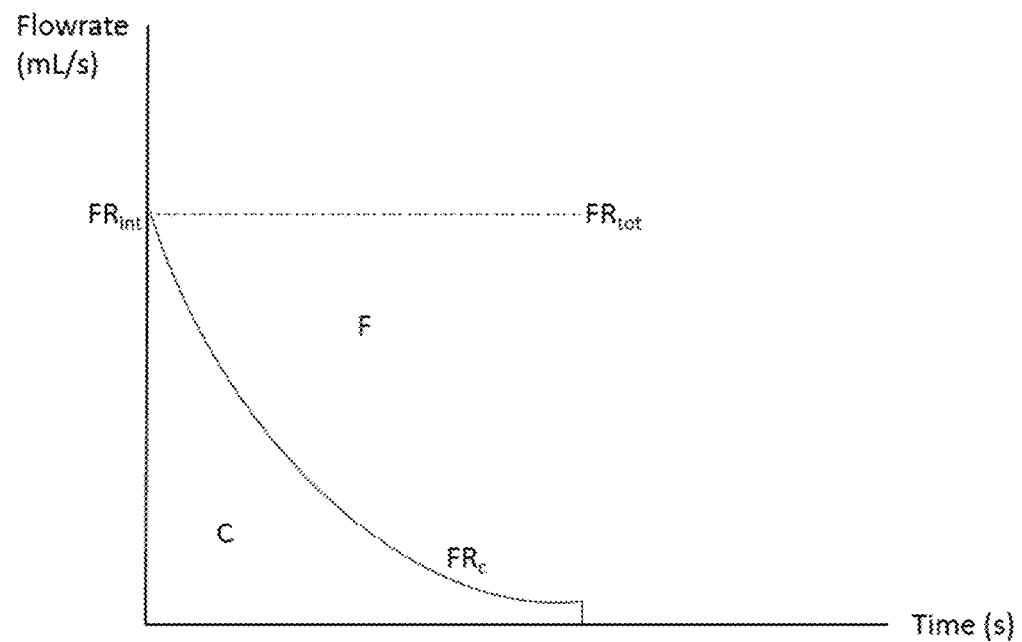
FIG. 2B is a graph of the injection profile according to FIG. 2A in which a consistent total volumetric flowrate is maintained through the addition of a flush fluid.

If the flowrate of contrast agent varies during the fluid delivery procedure or a phase thereof, as it does in the contrast agent protocols discussed above, maintaining a substantially consistent total volumetric flowrate of a fluid volume that includes both a contrast agent and a flush fluid during the procedure and/or phase requires varying the rate at which the flush fluid is delivered in a manner that is complementary to the variation in the flow of contrast. For example, if the contrast delivery protocol employs an exponentially decaying contrast flowrate, as illustrated in FIGS. 2A-2B, the flow rate of flush fluid would continually increase to maintain a substantially consistent total volumetric flowrate. This is illustrated in FIG. 2B, where the continually decreasing flowrate of contrast agent ($FR_c$) is countered with a continually increasing flow of flush fluid so that the total volumetric flowrate ($FR_{tot}$) of the fluid volume, where the fluid volume is made up of contrast and flush fluid, remains substantially consistent over the entire portion of the procedure depicted in FIG. 2B. In this example, the total volumetric flowrate ($FR_{tot}$) that is maintained is substantially the same as the initial total volumetric flowrate at the onset of the fluid delivery procedure ($FR_{int}$) which, in this example, consists entirely of contrast. The volume of contrast delivered is represented by the area "C" while the volume of flush fluid delivered is represented by the area "F."

Figure 3A:
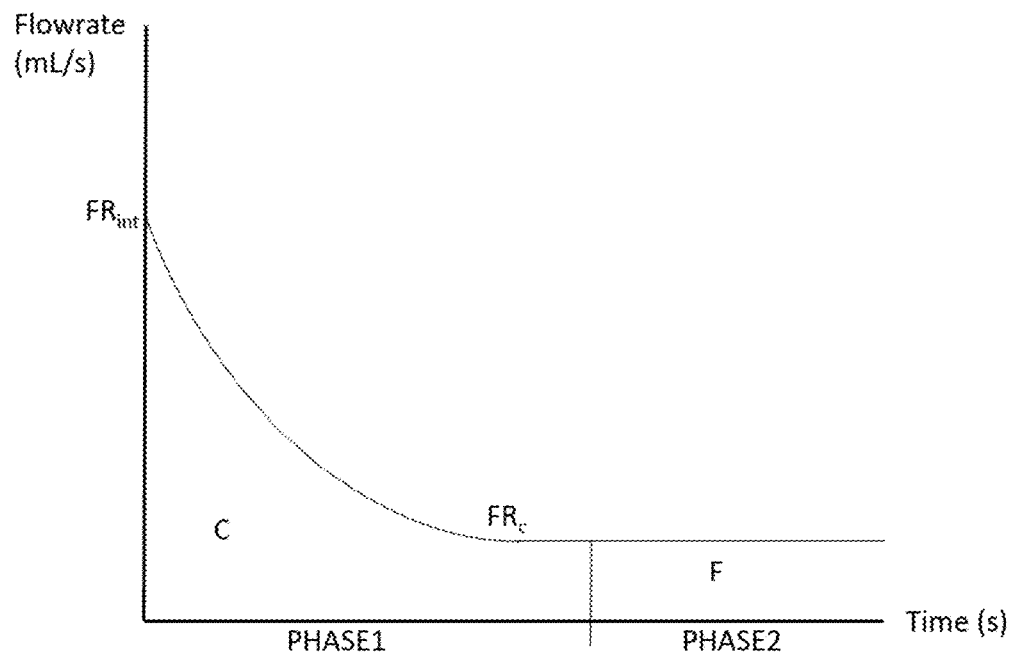
FIG. 3A is a graph of a two phase injection profile of a contrast agent according to one embodiment of Bae et al.
Figure 3B:
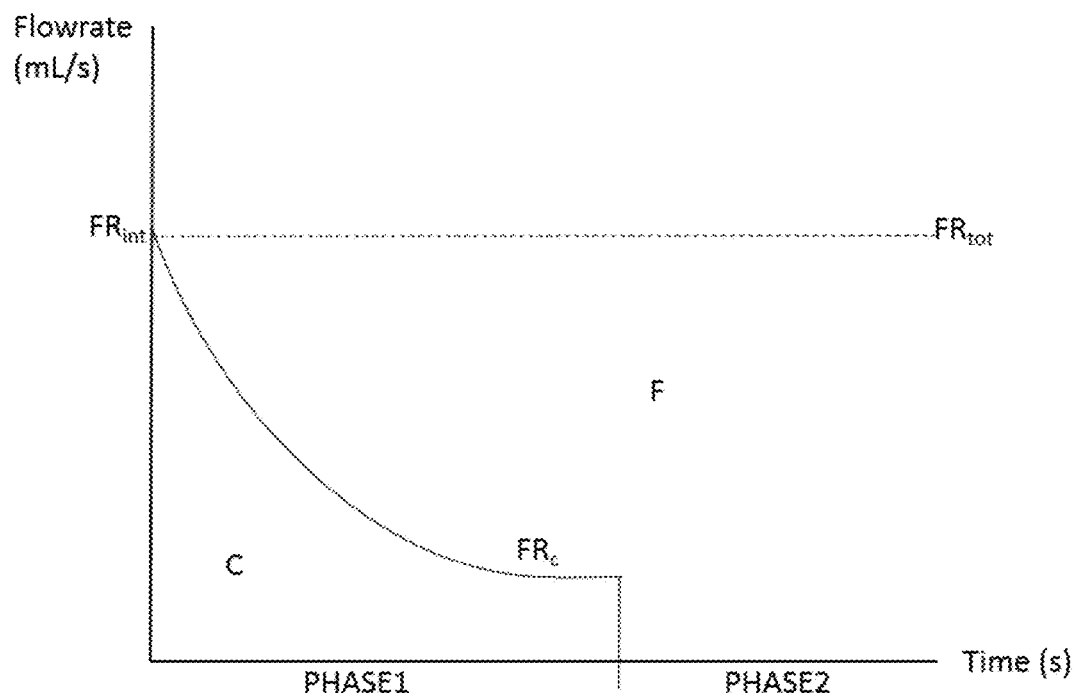
FIG. 3B is a graph of the injection profile according to FIG. 3A in which a consistent total volumetric flowrate is maintained through the addition of a flush fluid.

FIGS. 3A-3B provides another example of how the flow of flush fluid can be delivered in a two phase injection procedure which employs an exponentially decaying contrast flowrate in the first phase ("PHASE1") followed by a second phase ("PHASE2") consisting of only flush fluid. In the first phase, the total volumetric flowrate ($FR_{tot}$) throughout the phase is held equal to the initial total volumetric flowrate at the onset of the phase ($FR_{int}$) which, in this example, consists entirely of contrast. As the volumetric flowrate of the contrast agent ($FR_c$) decays exponentially throughout the first phase, as shown in FIG. 3B, a flush fluid is added at a rate that increases at the same rate that the flowrate of contrast is experiencing its decay. As shown in FIG. 3B, the result is a first phase in which the total volumetric flowrate ($FR_{tot}$) remains relatively consistent while the contrast flowrate ($FR_c$) is decaying from its initial rate, and the administration of flush fluid (e.g., saline) is increasing from zero. This is followed by a second phase in which only flush fluid is delivered at the same total volumetric flowrate ($FR_{tot}$). The illustration of FIG. 3B represents an improvement upon the bolus profile of FIG. 3A (which, as discussed above, represents the OptiBolus profile according to Mallinckrodt/Guerbet/Bae et al.). The fluid delivery procedure depicted in FIG. 3B adopts the consistent total volumetric flow approach of the present disclosure, which helps preserve the contrast bolus shape as the bolus traverses the peripheral vasculature. The volume of contrast delivered is represented by the area "C" while the volume of flush fluid delivered is represented by the area "F."

Figure 4B:
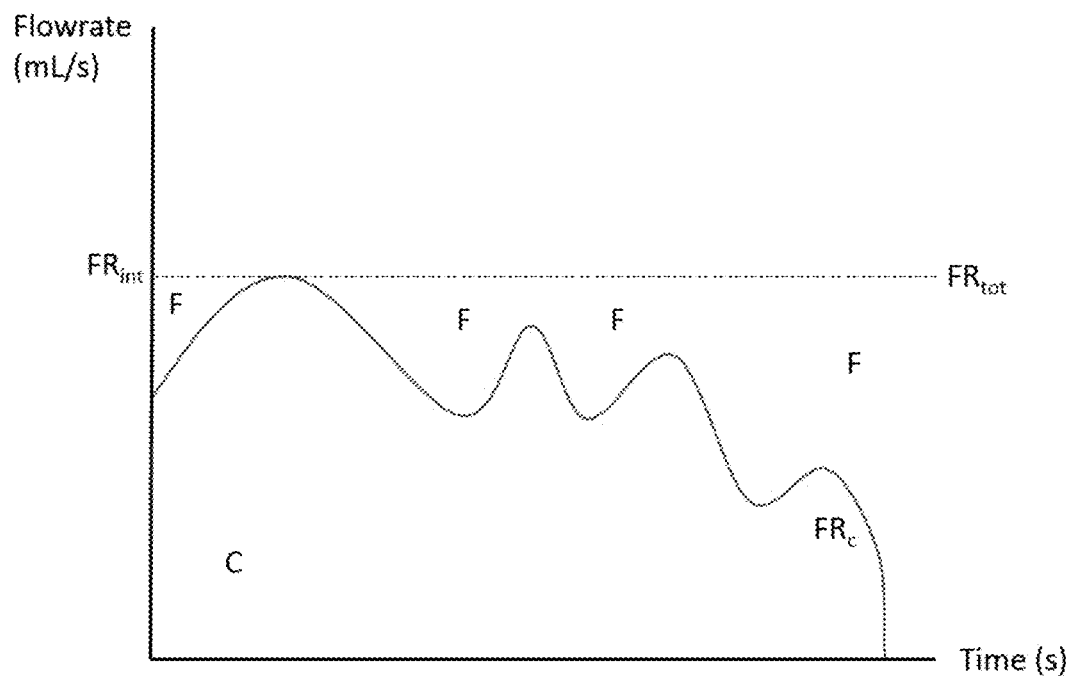
FIG. 4B is a graph of the injection profile according to FIG. 4A in which a consistent total volumetric flowrate is maintained through the addition of a flush fluid.

By way of another example, if the delivery of contrast follows a protocol in which the flow rate of contrast agent both increases and decreases during the injection procedure, flush fluid can be added at a volumetric flowrate that is complementary to the time varying rate at which the contrast agent is being simultaneously delivered. For instance, FIG. 4A illustrates an ideal contrast agent protocol developed under the method described by Fleischmann et al. As alluded to previously, the contrast agent protocol shown in FIG. 4A dictates that the contrast be administered to the patient according to a time-varying contrast flowrate ($FR_c$), and thus results in the contrast being injected at a continuously or semi-continuously varying volumetric flowrate over the duration of the contrast injection portion of the procedure. If such a contrast agent protocol is used, a flush fluid can be added over the course of the contrast injection so as to achieve a consistent total volumetric flowrate ($FR_{tot}$) and thus consistent delivery of the fluid volume, including the contrast agent, to the central circulation over the entire contrast injection procedure. This is illustrated in FIG. 4B. In this example, the flowrate of contrast agent ($FR_c$) and flush fluid both continuously vary, both upward and downward, during the contrast injection procedure so as to maintain a substantially consistent total volumetric flowrate ($FR_{tot}$). In this example, the total volumetric flowrate ($FR_{tot}$) is held equal to the initial total volumetric flowrate at the onset of the procedure ($FR_{int}$) and is preferably, but not necessarily, equal to or greater than the maximum flowrate of the contrast agent during the procedure. In this example, the initial total volumetric flowrate at the onset of the phase ($FR_{int}$) includes both a volumetric amount of contrast agent (C) and a volumetric amount of flush fluid (F). The illustration of FIG. 4B represents an improvement upon the bolus profile of FIG. 4A (which, as discussed above, represents the ideal profile according to Fleischmann et al.). The fluid delivery procedure depicted in FIG. 4B adopts the consistent total volumetric flow approach of the present disclosure, which helps preserve the contrast bolus shape as the bolus traverses the peripheral vasculature. The volume of contrast delivered is represented by the area "C" while the volume of flush fluid delivered is represented by the area "F."

Figure 4C:
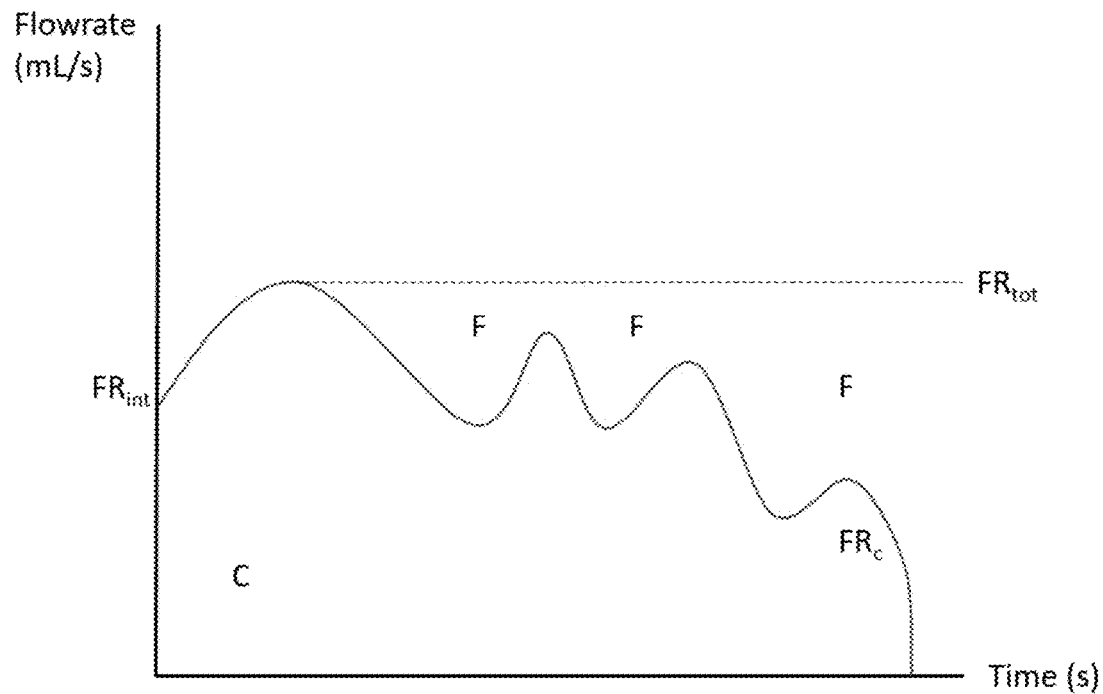
FIG. 4C is a graph of the injection profile according to FIG. 4B in which the initial flowrate is less than the total volumetric flowrate that is maintained through the addition of a flush fluid.

FIG. 4C represents a variation of FIG. 4B in which the total volumetric flowrate that is maintained ($FR_{tot}$) is higher than the initial total volumetric flowrate ($FR_{int}$) at the onset of the fluid delivery procedure. In this embodiment, the initial total volumetric flowrate ($FR_{int}$), which consists entirely of contrast agent, is increased through a gradual ramp up so that the total flowrate reaches the preselected total volumetric flowrate ($FR_{tot}$) which is then maintained. In this embodiment, flush fluid is added only after the total volumetric flowrate ($FR_{tot}$) is reached. The volume of contrast delivered is represented by the area "C" while the volume of flush fluid delivered is represented by the area "F."

Figure 5B:
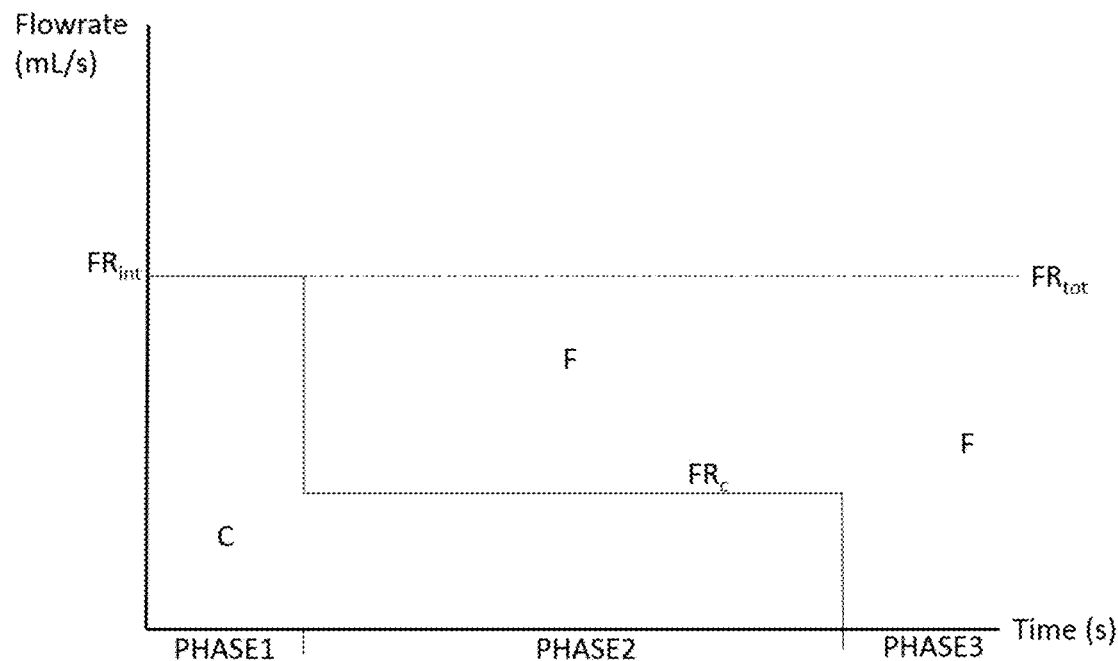
FIG. 5B is a graph of the injection profile according to FIG. 5A in which a consistent total volumetric flowrate is maintained through the addition of a flush fluid.

Another example is shown in FIGS. 5A-5B. In FIGS. 5A-5B, a first phase ("PHASE1") includes contrast agent administered as a relatively large rectangular bolus and a second phase ("PHASE2") in which contrast is administered as a smaller and longer bolus. The administration of contrast in this example is modeled after the normal Fleischmann et al. profile, discussed above. In the second phase ("PHASE2") of FIG. 5B, however, unlike the smaller contrast-only second phase shown in FIG. 5A, flush fluid is added to the injection so that the resulting admixture of contrast and flush fluid is delivered at the same total volumetric flowrate ($FR_{tot}$) as provided in the first contrast-only phase. This is followed by a third phase ("PHASE3") in which only flush fluid is injected at the same total volumetric flowrate ($FR_{tot}$), as shown in FIG. 5B. The illustration of FIG. 5B thus represents an optimized version of the normal bolus profile developed by Fleischmann et al., one in which a consistent total volumetric flow rate is used throughout the first contrast-only phase, the second admixture phase, and the third flush fluid-only phase. In this embodiment, the flowrate of the contrast agent is constant across each phase, and thus does not vary, across any particular phase of the procedure. The volume of contrast delivered is represented by the area "C" while the volume of flush fluid delivered is represented by the area "F."

Figure 6:
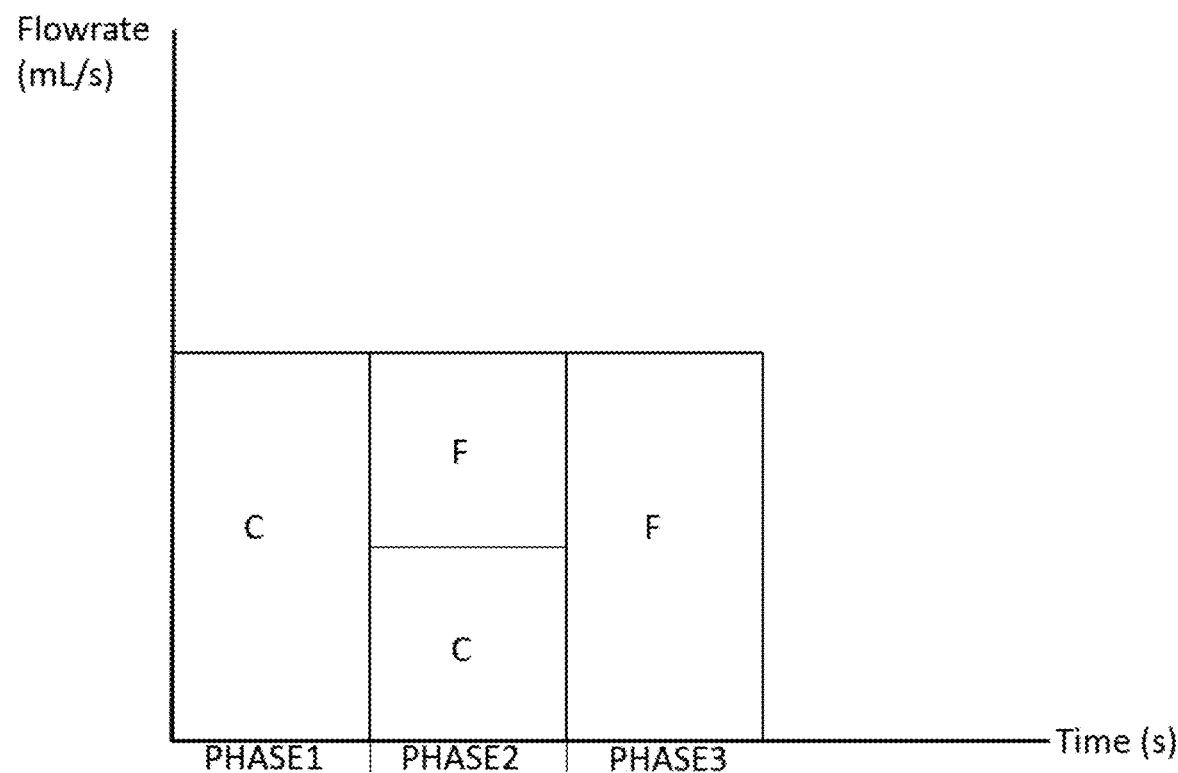
FIG. 6 is a graph of a three phase injection profile according to one embodiment of the Bayer P3T® protocol.

A comparison of FIG. 5B and FIG. 6 reveals that this optimized version of the normal Fleischmann et al. bolus profile yields a result similar in appearance to what can be accomplished using the P3T® software offered by Bayer, though the injection protocol or parameters of injection used in the Fleischmann et al. bolus are derived using a distinctly different methodology than in the P3T® software offered by Bayer.

Figure 4D:
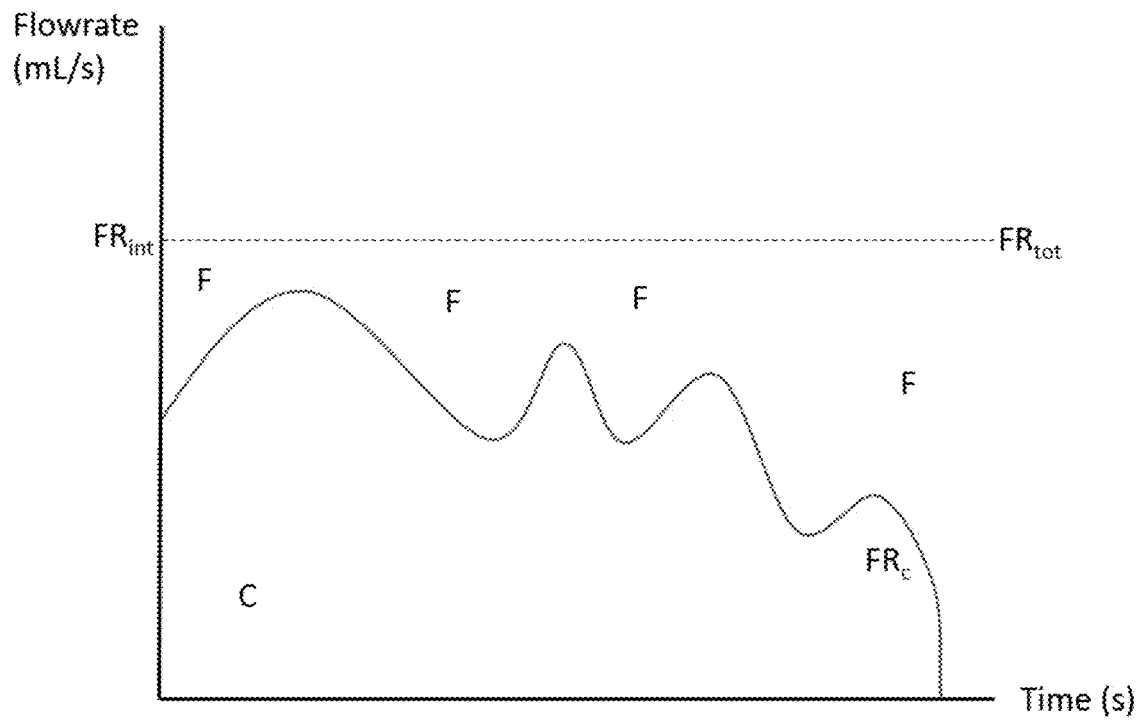
FIG. 4D is a graph of the injection profile according to FIG. 4A in which a consistent total volumetric flowrate that is higher than the contrast flowrate is maintained through the addition of a flush fluid.
Figure 5C:
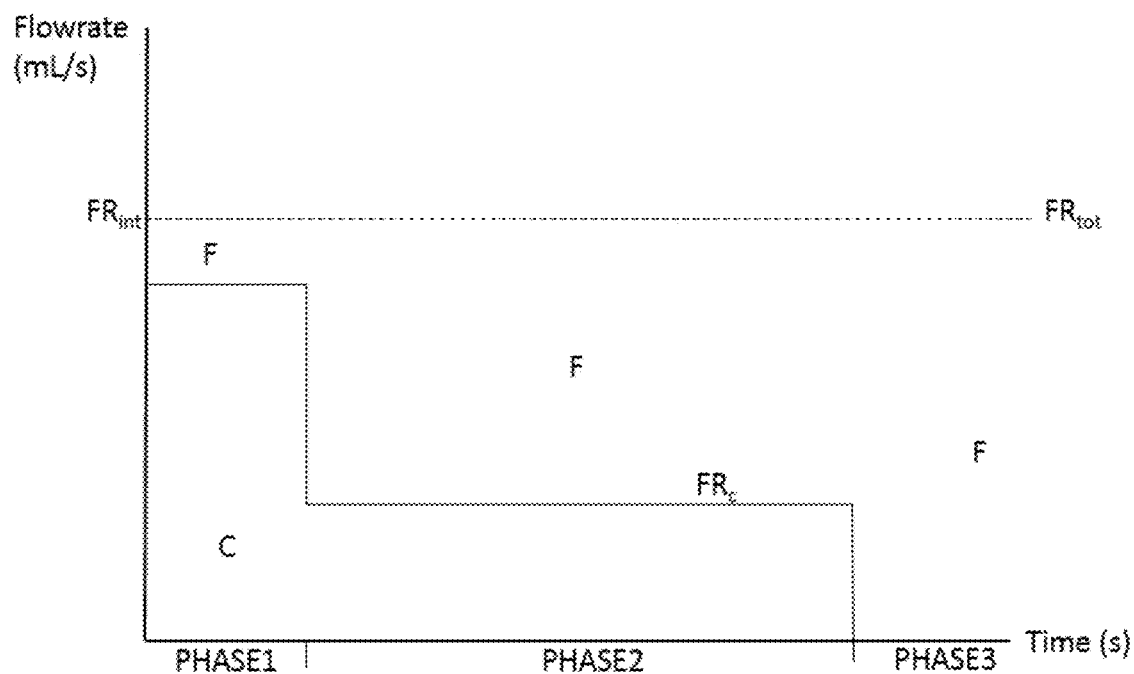
FIG. 5C is a graph of the injection profile according to FIG. 5A in which a consistent total volumetric flowrate that is higher than the contrast flowrate is maintained through the addition of a flush fluid.

In some situations or imaging studies, the flowrate of the contrast agent may be low compared to the flow of the blood in the patient's limb circulation, for example 0.1 ml/s of contrast agent. In this situation, it may be desirable to provide a total volumetric flowrate that is greater than the contrast flowrate over at least the entire period of time the contrast agent is being delivered, as shown in FIG. 4D and FIG. 5C, which are variations of FIG. 4C and FIG. 5B, respectively. For a normal adult, this desirable total volumetric flowrate may be, for example, on the order of 0.5 ml/s to 1 ml/s. For other body sizes, this may be scaled accordingly. By maintaining a total volumetric flowrate of this magnitude, the contrast agent and the flush fluid are moved expeditiously through the patient's veins into the central circulation. Without this additional flow, the veins may initially expand to hold the injected fluid volume and thus delay the transmission of the contrast agent to the central circulation and/or significantly distort the bolus shape or profile. Alternatively, if the veins are already fully distended, the veins may have large enough volumes that the normal venous flow is slow and injections at very low flowrates will result in a significant delay in the bolus arrival to the central circulation. By providing a higher total volumetric flowrate, the contrast agent and flush fluid are more quickly and predictably transmitted to the central circulation.

As discussed above, the variation of the flowrate of the flush fluid can be chosen so as to substantially maintain a preselected total volumetric flowrate even as the flowrate of the contrast agent varies. The protocol for delivering the flush fluid, including the flush fluid flowrate over time, can be determined by first determining the flow volume of the contrast agent at various points during the fluid delivery procedure or a portion thereof, as described above, and then subtracting the flowrate of the contrast agent from the total volumetric flowrate to ascertain the flow rate of the flush fluid needed at each of these points to reach the total volumetric flowrate. The calculated flowrate of the flush fluid can be used by controller 200 to control delivery of the flush fluid. Alternative means of determining the protocol for delivering the flush fluid are also available, including an algorithmic approach in which a protocol for delivering the flush fluid is developed based on the contrast agent protocol and the value of the total volumetric flowrate at each point in time, as would be understood by a person of skill in the art upon reading the present disclosure.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

The invention claimed is:

1. A method for delivering a medical fluid, comprising:
   delivering a fluid volume at a preselected total volumetric flowrate during a first duration of a fluid delivery procedure, wherein the fluid volume is comprised of a volumetric amount of a contrast agent and a volumetric amount of a flush fluid;
   controllably varying the volumetric amount of the contrast agent in the fluid volume during the first duration of the fluid delivery procedure, wherein the volumetric amount of the contrast agent is controllably decreased at an exponentially decaying rate during at least a portion of the first duration; and
   controllably varying the volumetric amount of the flush fluid in the fluid volume while the volumetric amount of the contrast agent is being controllably decreased so as to substantially maintain the preselected total volumetric flowrate throughout the first duration of the fluid delivery procedure,
   wherein the delivery of the contrast agent is substantially completed during the first duration.

2. The method of claim 1, wherein the method comprises delivering the medical fluid to a patient, and wherein the exponentially decaying rate decays according to a decay coefficient that is proportional to a cardiac output per body weight of the patient.

3. The method of claim 1, wherein the exponentially decaying rate decays according to a decay coefficient that is approximately 0.01 to 0.03.

4. The method of claim 1, wherein the volumetric amount of the contrast agent in the fluid volume is greater than zero during the first duration of the fluid delivery procedure.

5. The method of claim 1, wherein an initial total volumetric flowrate at an onset of the first duration consists entirely of contrast.

6. The method of claim 1, further comprising:
delivering a second fluid volume at a second preselected total volumetric flowrate during a second duration of the fluid delivery procedure, which is after the first duration, wherein the second fluid volume comprises a second volumetric amount of the flush fluid; and
maintaining the second preselected total volumetric flowrate throughout the second duration of the fluid delivery procedure.

7. The method of claim 6, wherein the second preselected total volumetric flowrate is substantially the same as the first preselected total volumetric flowrate.

8. The method of claim 6, wherein the second fluid volume consists entirely of the flush fluid.

9. The method of claim 6, wherein the second duration of the fluid delivery procedure immediately follows the first duration of the fluid delivery procedure.

10. The method of claim 6, wherein the fluid delivery procedure is substantially completed during the second duration.

11. The method of claim 1, further comprising:
delivering a second fluid volume at a second preselected total volumetric flowrate during a second duration, which is after the first duration of the fluid delivery procedure, wherein the second fluid volume is comprised of a second volumetric amount of the contrast and a second volumetric amount of the flush fluid;
controllably varying the second volumetric amount of the contrast agent in the second fluid volume during the second duration of the fluid delivery procedure; and
controllably varying the second volumetric amount of the flush fluid in the second fluid volume during the second duration of the fluid delivery procedure so as to substantially maintain the second preselected total volumetric flowrate throughout the second duration of the fluid delivery procedure.

12. The method of claim 11, wherein the second preselected total volumetric flowrate is substantially the same as the first preselected total volumetric flowrate.

13. The method of claim 11, wherein the second duration of the fluid delivery procedure immediately follows the first duration of the fluid delivery procedure.

14. A fluid delivery system, comprising:
a fluid administration device adapted to deliver a fluid volume, wherein the fluid volume comprises a volumetric amount of a contrast agent and a volumetric amount of a flush fluid; and
a controller in communication with the fluid administration device, wherein the controller comprises a processor and a non-transitory machine-readable storage medium, wherein the non-transitory machine-readable storage medium comprises instructions that, when executed by the processor, enable the fluid administration device to:
deliver the fluid volume at a preselected total volumetric flowrate during a first duration of a fluid delivery procedure;
controllably vary the volumetric amount of the contrast agent in the fluid volume during the first duration of the fluid delivery procedure, wherein the volumetric amount of the contrast agent is controllably decreased at an exponentially decaying rate during at least a portion of the first duration; and
controllably vary the volumetric amount of the flush fluid in the fluid volume while the volumetric amount of the contrast agent is being controllably decreased so as to substantially maintain the preselected total volumetric flowrate throughout the first duration of the fluid delivery procedure,
wherein the delivery of the contrast agent is substantially completed during the first duration.

15. The fluid delivery system of claim 14, further comprising a source of the contrast agent and a source of the flush fluid.

* * * * *